United States Patent
Nita (10) Patent No.: US 8,506,519 B2
(45) Date of Patent: Aug. 13, 2013

(54) PRE-SHAPED THERAPEUTIC CATHETER

(75) Inventor: Henry Nita, Redwood Shores, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 0 days.

(21) Appl. No.: 11/879,170

(22) Filed: Jul. 16, 2007

(65) Prior Publication Data

US 2007/0260172 A1 Nov. 8, 2007

Related U.S. Application Data (63) Continuation-in-part of application No. 11/711,970, filed on Feb. 27, 2007, now abandoned, which is a continuation of application No. 10/601,245, filed on Jun. 20, 2003, now abandoned, which is a continuation-in-part of application No. 10/211,418, filed on Aug. 2, 2002, now Pat. No. 6,855,123, and a continuation-in-part of application No. 10/251,227, filed on Sep. 20, 2002, now Pat. No. 6,702,748.

(51) Int. Cl.
*A61B 17/20* (2006.01)

(52) U.S. Cl.
USPC .................................................. 604/22

(58) Field of Classification Search
USPC .................... 604/523, 525, 532, 22
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,631,848 A | 1/1972 | Muller |
| 3,719,737 A | 3/1973 | Vaillancourt et al. |
| 3,823,717 A | 7/1974 | Pohlman et al. |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |
| 4,417,578 A | 11/1983 | Banko |
| 4,425,115 A | 1/1984 | Wuchinich |
| 4,486,680 A | 12/1984 | Bonnet et al. |

(Continued)

FOREIGN PATENT DOCUMENTS

| | | |
|---|---|---|
| DE | 2256127 | 5/1974 |
| DE | 2438648 | 2/1976 |

(Continued)

OTHER PUBLICATIONS

International Search Report dated Dec. 23, 2005 for PCT Application No. PCT/US2004/019378.

(Continued)

*Primary Examiner* — Bhisma Mehta
*Assistant Examiner* — Brandy S Lee
(74) *Attorney, Agent, or Firm* — Knobbe Martens Olson & Bear LLP (57) ABSTRACT

An ultrasound system has a catheter including an elongate flexible catheter body having a main lumen extending longitudinally therethrough. The catheter further includes an ultrasound transmission member extending longitudinally through the main lumen of the catheter body, the ultrasound transmission member having a proximal end connectable to an ultrasound generating device and a distal end coupled to the distal end of the catheter body. The catheter further includes a bent distal head or shaped a distal end of the catheter body to improve steerability.

13 Claims, 9 Drawing Sheets

(56) References Cited

U.S. PATENT DOCUMENTS

| | | | |
|---|---|---|---|
| 4,505,767 | A | 3/1985 | Quin |
| 4,565,589 | A | 1/1986 | Harrison |
| 4,572,184 | A | 2/1986 | Stohl et al. |
| 4,664,112 | A | 5/1987 | Kensey et al. |
| 4,665,906 | A | 5/1987 | Jervis |
| 4,679,558 | A | 7/1987 | Kensey et al. |
| 4,700,705 | A | 10/1987 | Kensey et al. |
| 4,721,117 | A | 1/1988 | Mar et al. |
| 4,750,902 | A | 6/1988 | Wuchinich et al. |
| 4,808,153 | A | 2/1989 | Parisi |
| 4,811,743 | A | 3/1989 | Stevens |
| 4,827,911 | A | 5/1989 | Broadwin et al. |
| 4,838,853 | A | 6/1989 | Parisi |
| 4,854,325 | A | 8/1989 | Stevens |
| 4,870,953 | A | 10/1989 | DonMicheal et al. |
| 4,920,954 | A | 5/1990 | Alliger et al. |
| 4,923,462 | A | 5/1990 | Stevens |
| 4,924,863 | A | 5/1990 | Sterzer |
| 4,931,047 | A | 6/1990 | Broadwin et al. |
| 4,936,281 | A | 6/1990 | Stasz |
| 4,936,845 | A | 6/1990 | Stevens |
| 5,000,185 | A | 3/1991 | Yock |
| 5,015,227 | A | 5/1991 | Broadwin et al. |
| 5,026,384 | A | 6/1991 | Farr et al. |
| 5,046,503 | A | 9/1991 | Schneiderman |
| 5,053,008 | A | 10/1991 | Bajaj |
| 5,058,570 | A | 10/1991 | Idemoto et al. |
| 5,076,276 | A | 12/1991 | Sakurai |
| 5,091,205 | A | 2/1992 | Fan |
| 5,100,423 | A | 3/1992 | Fearnot |
| 5,109,859 | A | 5/1992 | Jenkins |
| 5,114,414 | A | 5/1992 | Buchbinder |
| 5,116,350 | A | 5/1992 | Stevens |
| 5,127,917 | A | 7/1992 | Niederhauser et al. |
| 5,156,143 | A | 10/1992 | Bocquet et al. |
| 5,163,421 | A | 11/1992 | Bernstein |
| 5,180,363 | A | 1/1993 | Idemoto et al. |
| 5,183,470 | A | 2/1993 | Wettermann |
| 5,195,955 | A | 3/1993 | Don Michael |
| 5,215,614 | A | 6/1993 | Wijkamp et al. |
| 5,221,255 | A | 6/1993 | Mahurkar et al. |
| 5,226,421 | A | 7/1993 | Frisbie et al. |
| 5,234,416 | A | 8/1993 | Macaulay et al. |
| 5,238,004 | A | 8/1993 | Sahatjian et al. |
| 5,242,385 | A | 9/1993 | Strukel |
| 5,243,997 | A | 9/1993 | Uflacker et al. |
| 5,248,296 | A | 9/1993 | Alliger |
| 5,255,669 | A | 10/1993 | Kubota et al. |
| 5,267,954 | A | 12/1993 | Nita |
| 5,269,291 | A | 12/1993 | Carter |
| 5,269,297 | A | 12/1993 | Weng et al. |
| 5,269,793 | A | 12/1993 | Simpson |
| 5,287,858 | A | 2/1994 | Hammerslag et al. |
| 5,290,229 | A | 3/1994 | Paskar |
| 5,304,115 | A | 4/1994 | Pflueger et al. |
| 5,304,131 | A | 4/1994 | Paskar |
| 5,312,328 | A | 5/1994 | Nita et al. |
| 5,318,570 | A | 6/1994 | Hood et al. |
| 5,324,255 | A | 6/1994 | Passafaro et al. |
| 5,324,260 | A | 6/1994 | O'neill et al. |
| 5,325,860 | A | 7/1994 | Seward et al. |
| 5,326,342 | A | 7/1994 | Pflueger et al. |
| 5,328,004 | A | 7/1994 | Fannin et al. |
| 5,341,818 | A | 8/1994 | Abrams et al. |
| 5,342,292 | A | 8/1994 | Nita et al. |
| 5,344,395 | A | 9/1994 | Whalen et al. |
| 5,346,502 | A | 9/1994 | Estabrook et al. |
| 5,362,309 | A | 11/1994 | Carter |
| 5,368,557 | A | 11/1994 | Nita |
| 5,368,558 | A | 11/1994 | Nita |
| 5,376,084 | A | 12/1994 | Bacich et al. |
| 5,378,234 | A | 1/1995 | Hammerslag et al. |
| 5,380,274 | A | 1/1995 | Nita |
| 5,380,316 | A | 1/1995 | Aita et al. |
| 5,382,228 | A * | 1/1995 | Nita et al. .................. 604/22 |
| 5,383,460 | A | 1/1995 | Jang et al. |
| 5,389,096 | A | 2/1995 | Aita et al. |
| 5,397,293 | A | 3/1995 | Alliger et al. |
| 5,397,301 | A | 3/1995 | Pflueger et al. |
| 5,405,318 | A | 4/1995 | Nita |
| 5,409,483 | A | 4/1995 | Campbell et al. |
| 5,417,672 | A | 5/1995 | Nita et al. |
| 5,417,703 | A | 5/1995 | Brown et al. |
| 5,421,923 | A | 6/1995 | Clarke et al. |
| 5,427,118 | A | 6/1995 | Nita et al. |
| 5,431,168 | A | 7/1995 | Webster, Jr. |
| 5,431,663 | A | 7/1995 | Carter |
| 5,443,078 | A | 8/1995 | Uflacker |
| 5,447,509 | A | 9/1995 | Mills et al. |
| 5,449,369 | A | 9/1995 | Imran |
| 5,451,209 | A | 9/1995 | Ainsworth et al. |
| 5,465,733 | A | 11/1995 | Hinohara et al. |
| 5,474,531 | A | 12/1995 | Carter |
| 5,480,379 | A | 1/1996 | La Rosa |
| 5,484,398 | A | 1/1996 | Stoddard |
| 5,487,757 | A * | 1/1996 | Truckai et al. ............... 604/264 |
| 5,507,738 | A | 4/1996 | Ciervo |
| 5,516,043 | A | 5/1996 | Manna et al. |
| 5,527,273 | A | 6/1996 | Manna et al. |
| 5,540,656 | A * | 7/1996 | Pflueger et al. .................. 604/22 |
| 5,542,917 | A | 8/1996 | Nita et al. |
| 5,597,882 | A | 1/1997 | Schiller et al. |
| 5,607,421 | A | 3/1997 | Jeevanandam et al. |
| 5,611,807 | A | 3/1997 | O'Boyle |
| 5,618,266 | A | 4/1997 | Liprie |
| 5,626,593 | A | 5/1997 | Imran |
| 5,649,935 | A | 7/1997 | Kremer et al. |
| 5,658,282 | A | 8/1997 | Daw et al. |
| 5,695,460 | A | 12/1997 | Siegel et al. |
| 5,695,507 | A | 12/1997 | Auth et al. |
| 5,715,825 | A | 2/1998 | Crowley |
| 5,720,724 | A | 2/1998 | Ressemann et al. |
| 5,728,062 | A | 3/1998 | Brisken |
| 5,738,100 | A * | 4/1998 | Yagami et al. ............... 600/466 |
| 5,797,876 | A | 8/1998 | Spears et al. |
| 5,816,923 | A | 10/1998 | Milo et al. |
| 5,827,203 | A | 10/1998 | Nita |
| 5,830,222 | A | 11/1998 | Makower |
| 5,895,397 | A | 4/1999 | Jang et al. |
| 5,902,287 | A * | 5/1999 | Martin ........................ 604/532 |
| 5,935,142 | A | 8/1999 | Hood |
| 5,944,737 | A | 8/1999 | Tsonton et al. |
| 5,957,882 | A | 9/1999 | Nita et al. |
| 5,957,899 | A | 9/1999 | Spears et al. |
| 5,964,223 | A | 10/1999 | Baran |
| 5,967,984 | A | 10/1999 | Chu et al. |
| 5,971,949 | A | 10/1999 | Levin et al. |
| 5,976,119 | A | 11/1999 | Spears et al. |
| 5,989,208 | A * | 11/1999 | Nita ............................. 604/22 |
| 5,997,497 | A | 12/1999 | Nita et al. |
| 6,004,280 | A * | 12/1999 | Buck et al. .................... 600/585 |
| 6,007,499 | A | 12/1999 | Martin et al. |
| 6,007,514 | A | 12/1999 | Nita |
| 6,029,671 | A | 2/2000 | Stevens et al. |
| 6,030,357 | A | 2/2000 | Daoud et al. |
| 6,051,010 | A | 4/2000 | DiMatteo et al. |
| 6,113,558 | A | 9/2000 | Rosenschein et al. |
| 6,123,698 | A | 9/2000 | Spears et al. |
| 6,149,596 | A | 11/2000 | Bancroft |
| 6,165,127 | A | 12/2000 | Crowley |
| 6,165,188 | A | 12/2000 | Saadat et al. |
| 6,179,809 | B1 | 1/2001 | Khairkhahan et al. |
| 6,190,353 | B1 | 2/2001 | Makower et al. |
| 6,206,842 | B1 | 3/2001 | Tu et al. |
| 6,210,356 | B1 | 4/2001 | Anderson et al. |
| 6,217,543 | B1 | 4/2001 | Anis et al. |
| 6,231,546 | B1 | 5/2001 | Milo et al. |
| 6,231,587 | B1 | 5/2001 | Makower |
| 6,235,007 | B1 | 5/2001 | Divino, Jr. et al. |
| 6,241,692 | B1 | 6/2001 | Tu et al. |
| 6,241,703 | B1 | 6/2001 | Levin et al. |
| 6,277,084 | B1 | 8/2001 | Abele et al. |
| 6,283,983 | B1 | 9/2001 | Makower et al. |
| 6,287,271 | B1 | 9/2001 | Dubrul et al. |

| | | |
|---|---|---|
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,315,741 B1 | 11/2001 | Martin et al. |
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,450,975 B1 | 9/2002 | Brennan et al. |
| 6,454,757 B1 | 9/2002 | Nita et al. |
| 6,454,997 B1 | 9/2002 | Divino, Jr. et al. |
| 6,491,707 B2 | 12/2002 | Makower et al. |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,589,253 B1 | 7/2003 | Cornish et al. |
| 6,596,235 B2 | 7/2003 | Divino, Jr. et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,384,407 B2 | 6/2008 | Rodriguez et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,604,608 B2 | 10/2009 | Nita et al. |
| 7,621,929 B2 | 11/2009 | Nita et al. |
| 7,771,358 B2 | 8/2010 | Moehring et al. |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2005/0215946 A1 | 9/2005 | Hansmann et al. |
| 2005/0222557 A1 | 10/2005 | Baxter et al. |
| 2005/0228286 A1* | 10/2005 | Messerly et al. ............... 600/459 |
| 2006/0206039 A1 | 9/2006 | Wilson et al. |
| 2006/0264809 A1 | 11/2006 | Hansmann et al. |
| 2007/0037119 A1 | 2/2007 | Pal et al. |
| 2008/0108937 A1 | 5/2008 | Nita |
| 2011/0130834 A1 | 6/2011 | Wilson et al. |

FOREIGN PATENT DOCUMENTS

| | | |
|---|---|---|
| DE | 3821836 | 1/1990 |
| DE | 8910040 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0316796 | 11/1995 |
| EP | 0820728 | 1/1998 |
| GB | 1106957 | 3/1968 |
| JP | 01099547 | 4/1989 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| WO | WO89006515 | 7/1989 |
| WO | 9001300 | 2/1990 |
| WO | WO09001300 | 2/1990 |
| WO | 9004362 | 5/1990 |
| WO | 9107917 | 6/1991 |
| WO | WO92011815 | 7/1992 |
| WO | WO93008750 | 5/1993 |
| WO | 9316646 | 9/1993 |
| WO | WO94012140 | 6/1994 |
| WO | 9414382 | 7/1994 |
| WO | WO95008954 | 4/1995 |
| WO | WO95009571 | 4/1995 |
| WO | WO 95/15192 | 6/1995 |
| WO | WO96035469 | 11/1996 |
| WO | WO 97/21462 | 6/1997 |
| WO | WO97045078 | 12/1997 |
| WO | WO 98/052637 | 11/1998 |
| WO | WO99025412 | 5/1999 |
| WO | WO0053341 A1 | 9/2000 |
| WO | WO00/67830 | 11/2000 |
| WO | WO2004012609 | 2/2004 |
| WO | WO2004112888 | 12/2004 |
| WO | WO 2006/049593 | 5/2006 |

OTHER PUBLICATIONS

International Search Report dated Oct. 28, 2003 for PCT Application No. PCT/US2003/023468.

Office Action dated Aug. 3, 2010 from Japanese Application No. 2006-517355 filed on Jun. 16, 2004.

Office Action dated Jan. 26, 2010 from Japanese Application No. 2006-517355 filed on Jun. 16, 2004.

Supplemental European Search Report dated Nov. 5, 2009 for European Application No. EP03766931.

Siegel, et al., "In Vivo Ultrasound Arterial Recanalization of Atherosclerotic Total Occlusions", Journal of the American College of Cardiology, Feb. 1990, vol. 15, No. 2, pp. 345-351.

Extended European Search Report dated Mar. 5, 2012 for European Application No. 12153606.4.

Extended European Search Report dated Mar. 22, 2012 for European Application No. EP11188799.

Health Care Without Harm [report], Non-Incineration Medical Waste Treatment Technologies, "Irradiation, biological, and other technologies: E-beam, biological, and sharps treatment systems", Chapter 9., Aug. 2001, pp. 69-74.

* cited by examiner

PRE-SHAPED THERAPEUTIC CATHETER

RELATED CASES

This is a continuation-in-part of Ser. No. 11/711,970, filed Feb. 27, 2007, which is a continuation of Ser. No. 10/601,245, filed Jun. 20, 2003, now abandoned, which is a continuation-in-part of Ser. No. 10/211,418, filed Aug. 2, 2002, now U.S. Pat. No. 6,855,123, entitled "Therapeutic Ultrasound System", and Ser. No. 10/251,227, filed Sep. 20, 2002, now U.S. Pat. No. 6,702,748, entitled "Connector For Securing Ultrasound Catheter to Transducer", the entire disclosures of which are incorporated by this reference as though set forth fully herein.

BACKGROUND OF THE INVENTION

1. Field of the Invention

The present invention pertains to medical equipment, and more particularly, to a therapeutic ultrasound system and methods used therewith for ablating obstructions within tubular anatomical structures such as blood vessels.

2. Description of the Prior Art

A number of ultrasound systems and devices have heretofore been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, requires the use of relatively small diameter ultrasound catheters which are sufficiently small and flexible to undergo transluminal advancement through the tortuous vasculature of the aortic arch and coronary tree. However, all of these systems and devices generally encounter some problems.

A first type of problem relates generally to the effective transmission of ultrasound energy from an ultrasound source to the distal tip of the device where the ultrasound energy is applied to ablate or remove obstructive material. Since the ultrasound source, such as a transducer, is usually located outside the human body, it is necessary to deliver the ultrasound energy over a long distance, such as about 150 cm, along an ultrasound transmission wire from the source to the distal tip. Attenuation of the acoustical energy along the length of the transmission wire means that the energy reaching the distal tip is reduced. To ensure that sufficient energy reaches the distal tip, a greater amount of energy must be delivered along the transmission wire from the source to the distal tip. This transmission of increased energy along the transmission wire may increase the fatigue experienced by the transmission wire at certain critical locations, such as at the connection between the transducer and the transmission wire.

A second type of problem relates to the breakage of the ultrasound transmission member which extends through such catheters. Because of its small diameter, the ultrasound transmission member is particularly susceptible to breakage. Breakage of an ultrasound transmission member typically occurs near the proximal end thereof, generally within a few ultrasound nodes of the interface of the ultrasound catheter coupling and the ultrasound transducer coupling. This is believed to be because energy concentrations are highest at these points. In addition, significant amounts of heat can build up along the length of the ultrasound transmission member, and excessive heat can damage the integrity of the ultrasound transmission member.

A third type of problem relates to the need for accurately positioning the ultrasound device inside a patient's vasculature, and in particular, where the vasculature contains smaller and more tortuous vessels. To address this need, flexible and low-profile ultrasound devices have been provided which allow the device to be navigated through small and tortuous vessels. However, these devices have not been completely satisfactory in meeting these navigational needs.

A fourth type of problem relates to the actual ablation of the obstructive material. During the ultrasound procedure, the distal tip of the catheter is displaced to ablate the obstructive material. In this regard, it is desirable to have this displacement of the distal tip be operating in an optimum manner.

A fifth type of problem relates to the removal of particles that are produced when the obstructive material is ablated or broken up. It is important that these particles be removed from the patient's vascular system to avoid distal embolization and other clinical complications.

Thus, there still exists a need for improved ultrasound systems having ultrasound devices or catheters which address the aforementioned problems.

SUMMARY OF THE DISCLOSURE

The terms "ultrasound transmission wire" and "ultrasound transmission member" shall be used interchangeably herein, and are intended to mean the same element.

It is an object of the present invention to provide an ultrasound device that provides an improved connection between the ultrasound transmission member and the transducer.

It is another object of the present invention to provide an ultrasound device that minimizes breakage of the ultrasound transmission member.

It is yet another object of the present invention to provide an ultrasound device that can effectively navigate smaller and more tortuous vessels.

It is yet another object of the present invention to provide an ultrasound device that provides the clinician with enhanced visibility of the site of the obstructive material.

It is yet another object of the present invention to provide a catheter tip for an ultrasound device that can improve the displacement of the tip during ablation of the obstructive material.

It is yet another object of the present invention to provide an ultrasound device that effectively removes particles from the patient's vascular system.

In order to accomplish the objects of the present invention, there is provided an ultrasound system having a catheter including an elongate flexible catheter body having a main lumen extending longitudinally therethrough. The catheter further includes an ultrasound transmission member extending longitudinally through the main lumen of the catheter body, the ultrasound transmission member having a proximal end connectable to an ultrasound generating device and a distal end coupled to the distal end of the catheter body.

According to one embodiment of the present invention, a guidewire lumen extends longitudinally through a portion of the main lumen and terminates in a guidewire port that is closer to the proximal end of the catheter body than the distal end of the catheter body. The guidewire lumen can be defined by a guidewire tube that can be positioned at about the center of the main lumen.

According to another embodiment of the present invention, a distal head is connected to the distal end of the catheter body, the distal head being made from low-density material that is rigid and radio-dense.

According to another embodiment of the present invention, the catheter has a distal tip having a bore with a proximal section and a distal section that has an inner diameter that is smaller than the diameter of the proximal section of the bore. A guidewire lumen extends longitudinally through a portion of the main lumen, and into the proximal section of the bore of the distal tip, the guidewire lumen terminating before the distal section of the bore of the distal head.

The present invention also provides a method of reverse irrigation where the tissue particles are carried with cooling fluid through the main lumen of the catheter from the distal tip to the proximal end to be removed outside the blood vessel. This use of reverse irrigation allows for tissue particle removal and for simultaneous cooling of the ultrasound transmission member.

The present invention also provides a method of locally imaging a treatment location during a medical procedure using contrast media.

The present invention also provides a method of shaping the distal end of a catheter, which can be accomplished by maintaining the distal end of the catheter in a bent configuration over a heat source for a period of time, and then cooling the distal end. Alternatively, the shaping of the distal end of a catheter can also be accomplished by shaping or forming the distal end of the ultrasound transmission member separately, prior to the final assembly of the catheter, using a variety of methods including mechanical bending or bending and heating. Once the ultrasound transmission member has been pre-shaped at a desired angle, it is placed inside the catheter body. Additionally, the distal end of the catheter body may be pre-shaped prior to placement of the ultrasound transmission member. As a further alternative, shaping of the distal head of the ultrasound catheter can be done by utilizing a longer head element attached to the distal end of the ultrasound transmission member and shaping the head of the ultrasound catheter at a desired angle. According to yet another embodiment of the present invention, the distal end of the ultrasound transmission member serves as the distal head.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
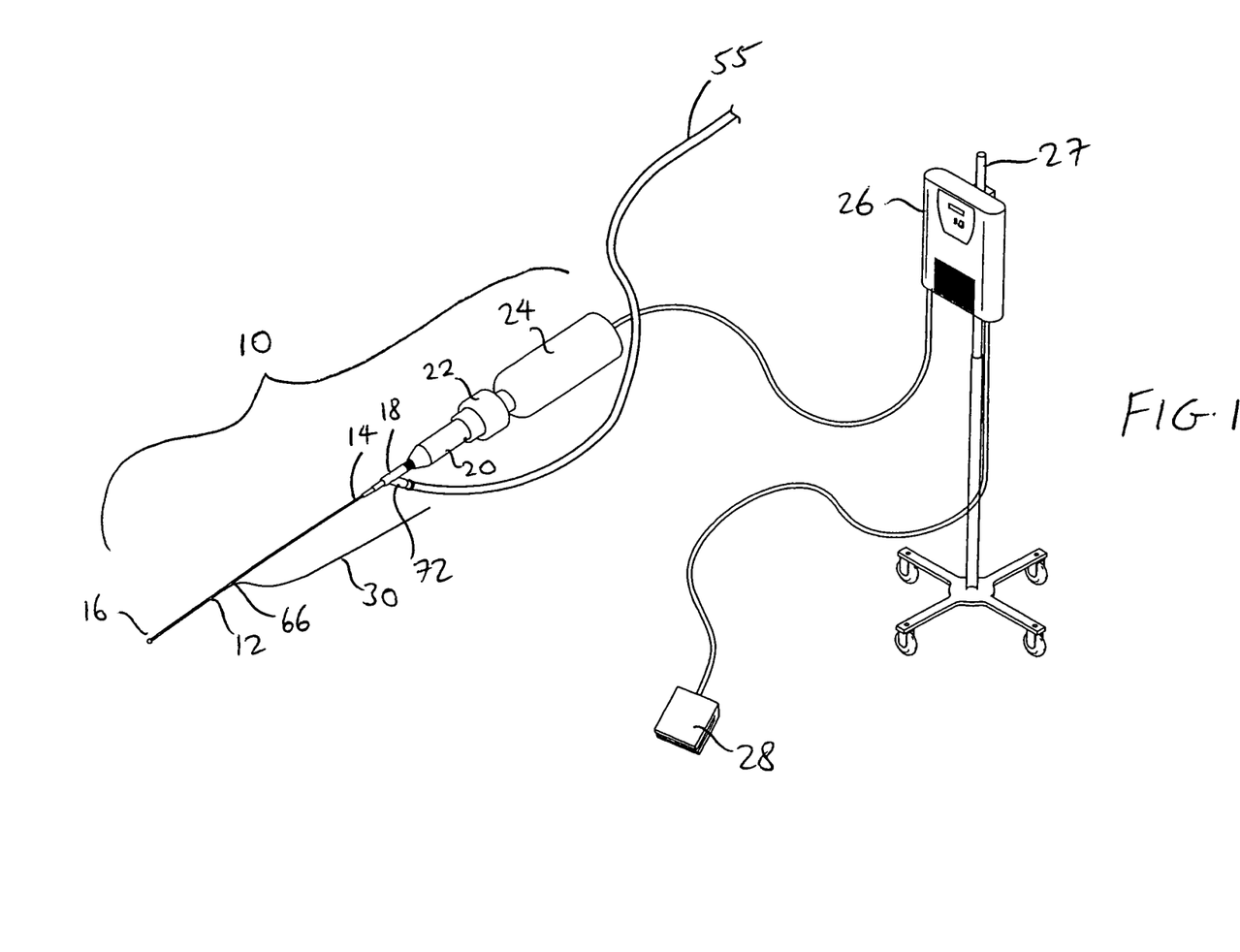
FIG. 1 is a perspective view of an ultrasound system according to the present invention.
Figure 2:
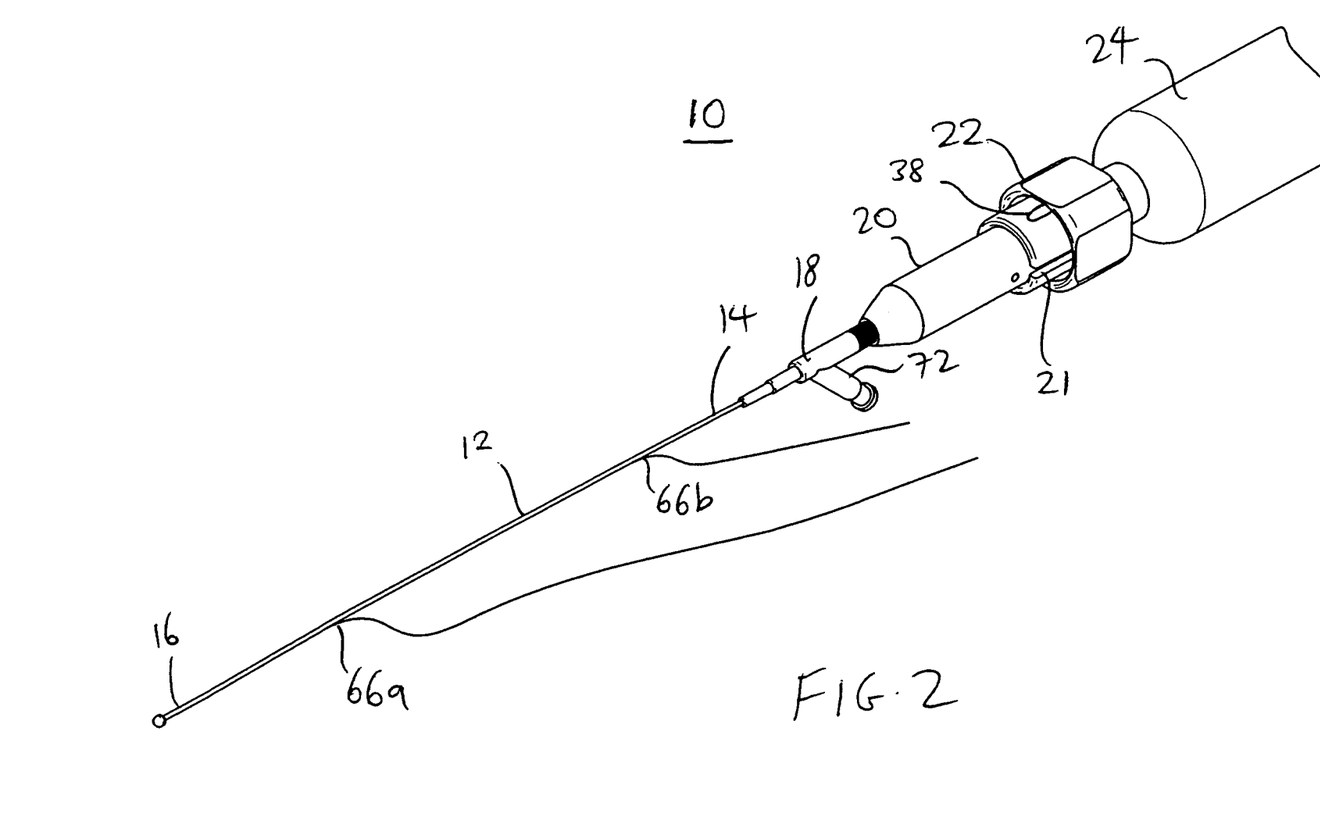
FIG. 2 is a perspective view of an ultrasound catheter that can be used with the system shown in FIG. 1.

FIGS. 1 and 2 illustrate an ultrasound system according to the present invention for use in ablating and removing occlusive material inside the vessel of an animal or human being. The ultrasound system includes an ultrasonic catheter device 10 which has an elongate catheter body 12 having a proximal end 14, a distal end 16, and defining at least one lumen extending longitudinally therethrough. The ultrasound catheter device 10 is operatively coupled at its proximal end 14, by way of a Y-connector 18, a catheter knob 20, and a slide collar 22, to an ultrasound transducer 24. The ultrasound transducer 24 is connected to a signal generator 26, which can be provided with a foot actuated on-off switch 28. The signal generator 26 can be supported by an IV pole 27. When the on-off switch 28 is depressed, the signal generator 26 sends an electrical signal to the ultrasound transducer 24, which converts the electrical signal to ultrasound energy. Such ultrasound energy subsequently passes through the catheter device 10 and is delivered to the distal end 16. A guidewire 30 may be utilized in conjunction with the catheter device 10, as will be more fully described below.

FIGS. 3A, 3B, 4A and 4B illustrate two non-limiting configurations for the distal end 16 of the catheter body 12 of the catheter device 10. The same numeral designations will be utilized in FIGS. 3A-4B to illustrate the same elements and to avoid repetition in this disclosure. The catheter body 12 is formed of a flexible polymeric material such as nylon (Pebax™) manufactured by Atochimie, Cour be Voie, Hauts Ve-Sine, France. The flexible catheter body 12 is preferably in the form of an elongate tube having one or more lumens extending longitudinally therethrough. The catheter body 12 defines a main lumen 40. Extending longitudinally through the main lumen 40 is an elongate ultrasound transmission member 42 having a proximal end which is removably connectable to the ultrasound transducer 24 such that ultrasound energy will pass through the ultrasound transmission member 42. As such, when the foot actuated on-off switch 28 operatively connected to the ultrasound transducer 24 is depressed, ultrasound energy will pass through the ultrasound transmission member 42 to the distal end 16 of the catheter body 12.

A distal head 44 is affixed to the distal end 16 of the catheter body 12. In the embodiments shown, the distal head 44 has a generally blunt distal tip 46, and has a proximal portion 48 whose outer diameter is slightly less than the largest outer diameter of the distal head 44, so as to define an annular shoulder 50 that is placed in the open distal end 52 of the catheter body 12 such that the proximal portion 48 of the distal head 44 is received inside the catheter body 12.

The distal head 44 is preferably formed of a material that is rigid, is radio-dense, and has low-density. A material having such characteristics is desirable because the ultrasound energy that is delivered from a transducer 24 to the distal head 44 via the ultrasound transmission member 42 goes through severe bends in the patient's vasculature. These bends significantly impact the displacement at the distal head 44 and its ability to ablate atherosclerotic plaque. The distal head 44 provides an additional load so that a heavier distal head 44 will cause lower displacements. As a result, a distal head 44 made of a material that is rigid, is radio-dense, and which has low-density will improve the effectiveness of the ablation. As a non-limiting example, the material should have an average density that does not exceed 5 g/cm$^3$, or where the total mass of the distal head 44 does not exceed 0.015 grams.

As for the desired materials, Titanium alloys are preferable because they have the highest strength-to-weight ratios of any structural metals, and are corrosion resistant and biocompatible. Pure Titanium has a density of 0.163 lb/in$^3$. Examples of desirable alloy elements for use with Titanium include Aluminum and Vanadium, such as in Ti-6Al-4V, which has tensile yield strength in the range of 130-150 ksi.

Although pure Aluminum is relatively weak, alloying with various elements yields significant strength improvements with minimal sacrifice in density. Pure Aluminum has a density of 0.097 lb/in$^3$. Examples of desirable alloying elements for Aluminum include Manganese, Silicon, and/or Magnesium, such as in 3, 4, 5 and 6 series Aluminum alloys. Tensile yield strengths of these common alloys range from 10-50 ksi.

Magnesium alloys are also preferable because they are extremely light, stable, abundant, and easy to machine. They have high specific strength and rigidity, with a very low density range of 0.064-0.066 lb/in$^3$, and UTS range of 22-55 ksi. Examples of desirable alloying elements that can be used with Magnesium include Aluminum and Zinc, such as in AZ31B for machined tips, or Zinc and rare-earth elements or Zirconium such as in ZE63A or ZK61A for cast tips.

Various structural or engineering polymers may make desirable tip materials, due to inherently low densities yet high impact strength and rigidity. Examples of desirable plastics include ABS, Polycarbonate, Polyphenylene Oxide, Polyarylate, Polysulfone or any alloys thereof.

Figure 3A:
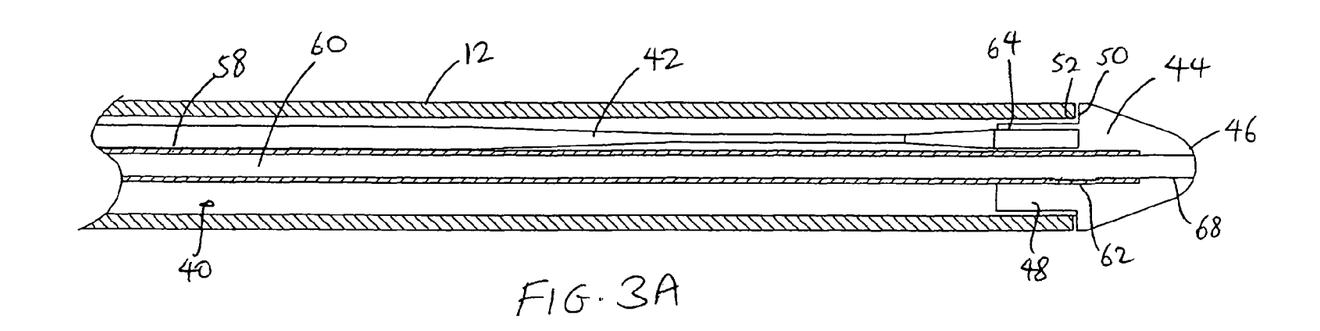
FIG. 3A is a cross-sectional view of the distal end of the ultrasound catheter of FIG. 2 according to one embodiment thereof.
Figure 3B:
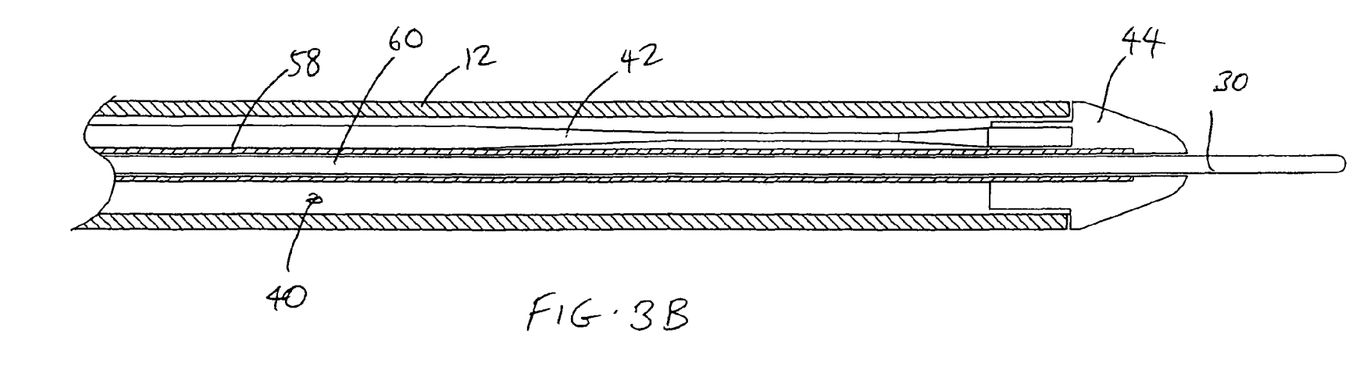
FIG. 3B is a cross-sectional view of the distal end of the ultrasound catheter of FIG. 3A shown with the guidewire extending through the guidewire lumen.

In addition, a guidewire tube 58 defining a guidewire lumen 60 extends through the main lumen 40 and a central bore formed through the distal head 44. In the present invention, the guidewire tube 58 and its lumen 60 are positioned at a central location within the main lumen 40 and the distal head 44, instead of being located eccentrically inside the main lumen 40. FIGS. 3B and 4B illustrate a guidewire 30 extending through the guidewire lumen 60. Providing the guidewire tube 58 and its lumen 60 at a central location in the main lumen 40 will allow for improved movement of the catheter 10 over the guidewire 64.

The guidewire tube 58 can be bonded or attached to the central bore of the distal head 44 using attachment or bonding methods that are well-known in the catheter art. FIGS. 3A-3B and 4A-4B illustrate two different ways of connecting the guidewire tube 58 inside the distal head 44. In one embodiment as shown in FIGS. 3A and 3B, the central bore has a proximal section 62, and a distal section 68 that opens at the distal tip 46. The proximal section 62 has a larger internal diameter than the distal section 68, but the internal diameter of the distal section 68 is sized to be about the same as the internal diameter of the guidewire lumen 60. Thus, the internal diameter of the proximal section 62 is sized to be about the same as the outer diameter of the guidewire tube 58, so as to snugly receive the distal end of the guidewire tube 58 inside the proximal section 62. By providing the internal diameter of the distal section 68 to be about the same as the internal diameter of the guidewire lumen 60, a smooth dimensional transition can be provided for movement of the guidewire 30. In addition, by terminating the distal end of the guidewire tube 58 before the distal tip 46 of the distal head 44, the material (i.e., usually plastic) of the guidewire tube 58 need not contact the atherosclerotic material during ablation, thereby improving the effectiveness of the ablation. This is because the plastic material of the guidewire tube 58 is not as effective in ablating atherosclerotic material.

Figure 4A:
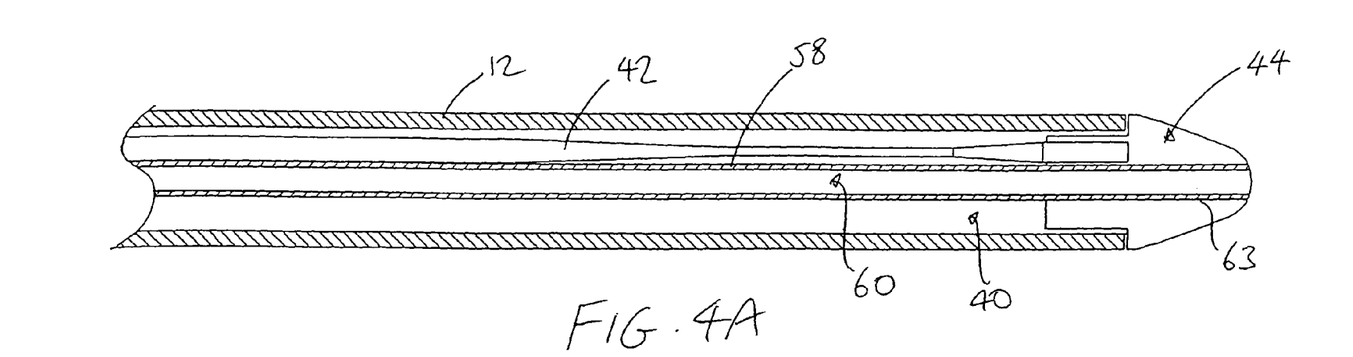
FIG. 4A is a cross-sectional view of the distal end of the ultrasound catheter of FIG. 2 according to another embodiment thereof.
Figure 4B:
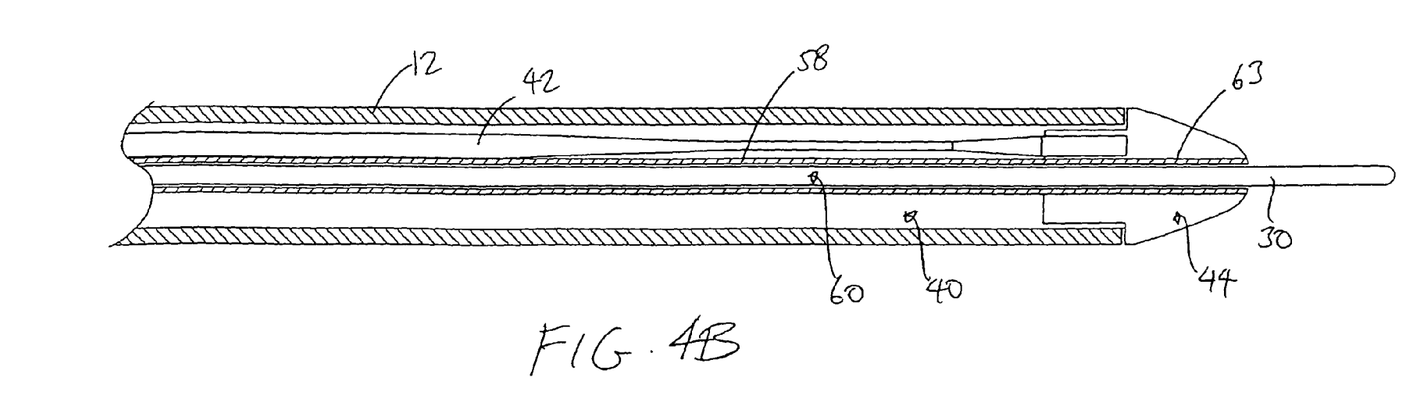
FIG. 4B is a cross-sectional view of the distal end of the ultrasound catheter of FIG. 4A shown with the guidewire extending through the guidewire lumen.

In another embodiment as shown in FIGS. 4A and 4B, the central bore 63 has the same internal diameter throughout its length in the distal head 44, and the guidewire tube 58 extends through the entire distal head 44 along its concentric longitudinal axis.

The guidewire tube 58 can extend along the length of the catheter body 12 if the catheter device 10 is an "over-the-wire" catheter device. If the catheter device 10 is a "monorail" catheter device, as shown in FIG. 1, the guidewire tube 58 terminates at a guidewire aperture 66 that is positioned along the length of the catheter body 12, at which the guidewire 30 exits the catheter body 12 (as shown in FIG. 1). Referring to FIG. 2, the guidewire aperture 66 can be provided at a variety of different locations along the length of the catheter body 12. For example, one possible location 66a can be adjacent but slightly proximal from the distal end 16 of the catheter body 12. As another example, another possible location 66b can be adjacent but slightly distal from the Y-connector 18.

The different locations 66a, 66b for the guidewire aperture provide different benefits and disadvantages, and their uses will depend on the desired applications and the personal preferences of the clinician. For example, if the aperture 66 is closer to the distal end 16, it is assumed that the aperture 66 would be positioned inside the vasculature of the patient when in use. In such a situation, the clinician can exchange catheters or other devices over the guidewire without losing the position of the guidewire. However, this situation suffers from the drawback that it is not possible to exchange guidewires because the aperture 66 is positioned inside the vasculature. As another example, if the aperture 66 is adjacent but slightly distal from the Y-connector 18, it is assumed that the aperture 66 would be positioned outside the body of the patient when in use. In such a situation, the clinician can still exchange catheters or other devices over the guidewire, but a longer guidewire will be needed. In addition, guidewire exchange can be easily facilitated. However, this situation suffers from the drawback that it will be more difficult for the clinician to operate and manipulate the catheter and guidewire during a procedure.

The ultrasound transmission member 42 extends through the main lumen 40 and is inserted into a bore 64 which extends longitudinally into the proximal portion 48 of the distal head 44. The distal end of the ultrasound transmission member 42 is firmly held within the bore 64 by the frictional engagement thereof to the surrounding material of the distal head 44, or by other mechanical or chemical affixation means such as but not limited to weldments, adhesive, soldering and crimping. Firm affixation of the ultrasound transmission member 42 to the distal head 44 serves to facilitate direct transmission of the quanta of ultrasonic energy passing through the ultrasound transmission member 42 to the distal head 44. As a result, the distal head 44, and the distal end 16 of the catheter device 10, are caused to undergo ultrasonic vibration in accordance with the combined quanta of ultrasonic energy being transmitted through the ultrasound transmission member 42.

In the preferred embodiment, the ultrasound transmission member 42 may be formed of any material capable of effectively transmitting the ultrasonic energy from the ultrasound transducer 24 to the distal head 44, including but not necessarily limited to metal, hard plastic, ceramic, fiber optics, crystal, polymers, and/or composites thereof. In accordance with one aspect of the invention, all or a portion of the ultrasound transmission member 42 may be formed of one or more materials which exhibit super-elasticity. Such materials should preferably exhibit super-elasticity consistently within the range of temperatures normally encountered by the ultrasound transmission member 42 during operation of the catheter device 10. Specifically, all or part of the ultrasound transmission member 30 may be formed of one or more metal alloys known as "shape memory alloys".

Examples of super-elastic metal alloys which are usable to form the ultrasound transmission member 42 of the present invention are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 42 of the present invention operates, any and all of which super-elastic metal alloys may be usable to form the super-elastic ultrasound transmission member 42.

The frontal portion of the Y-connector 18 is connected to the proximal end 14 of the catheter 10 using techniques that are well-known in the catheter art. An injection pump (not shown) or IV bag (not shown) or syringe (not shown) can be connected, by way of an infusion tube 55, to an infusion port or sidearm 72 of the Y-connector 18. The injection pump can be used to infuse coolant fluid (e.g., 0.9% NaCl solution) into and/or through the main lumen 40 of the catheter 10. Such flow of coolant fluid may be utilized to prevent overheating of the ultrasound transmission member 42 extending longitudinally through the main lumen 40. Such flow of the coolant fluid through the main lumen 40 of the catheter 10 serves to bathe the outer surface of the ultrasound transmission member 42, thereby providing for an equilibration of temperature between the coolant fluid and the ultrasound transmission member 42. Thus, the temperature and/or flow rate of coolant fluid may be adjusted to provide adequate cooling and/or other temperature control of the ultrasound transmission member 42. For example, the coolant temperature at the distal end 16 of the catheter 10 is preferably in the range of 35-44 degrees Celcius, and is preferably less than 50 degrees Celcius, since tissue de-naturalization normally occurs around 50 degrees Celcius.

In addition to the foregoing, the injection pump or syringe may be utilized to infuse a radiographic contrast medium into the catheter 10 for purposes of imaging, as described in greater detail below. Examples of iodinated radiographic contrast media which may be selectively infused into the catheter 10 via the injection pump are commercially available as Angiovist 370 from Berlex Labs, Wayne, N.J. and Hexabrix from Malinkrodt, St. Louis, Mo.

The proximal end of the Y-connector 18 is attached to the distal end of the catheter knob 20 by threadably engaging the proximal end of the Y-connector 18 inside a threaded distal bore (e.g., see 88 in FIGS. 5 and 6) at the distal end of the catheter knob 20. The proximal end of the catheter knob 20 is received by the sleeve 80 and the distal end of the transducer housing 82. The sleeve 80 is positioned over the distal end of the transducer housing 82, and overlaps the catheter knob 20. A slidable collar 22 is positioned over the sleeve 80. The collar 22 has a non-supporting position where the collar 22 is retracted towards the housing 82 of the transducer 24, and has a supporting position where the collar 22 is extended over the sleeve 80. The sleeve 80 has an open-ended slot 21 (see FIG. 2). Alternatively, the sleeve can have a close-ended slot 38, or any number of close-ended slots 38 and open-ended slots 21 in any combination thereof. The collar 22 has a tapered internal bore 36, and when moved to the supporting position, the collar 22 is disposed around the sleeve 80 and compresses the sleeve 80 to provide a grip. The collar 22 may also have a countersink 34 that facilitates movement from the non-supporting position to the supporting position. The collar 22 functions as a support member that is disposed on the housing 82 of the transducer 24 to support at least a portion of the catheter knob 20. Support of the catheter knob 20 with the sleeve 80 and the collar 22 reduces mechanical stress applied to the connection area between the transducer 24 and the ultrasound transmission member 42, and reduces fatigue and potential breakage of the ultrasound transmission member 42.

Figure 5:
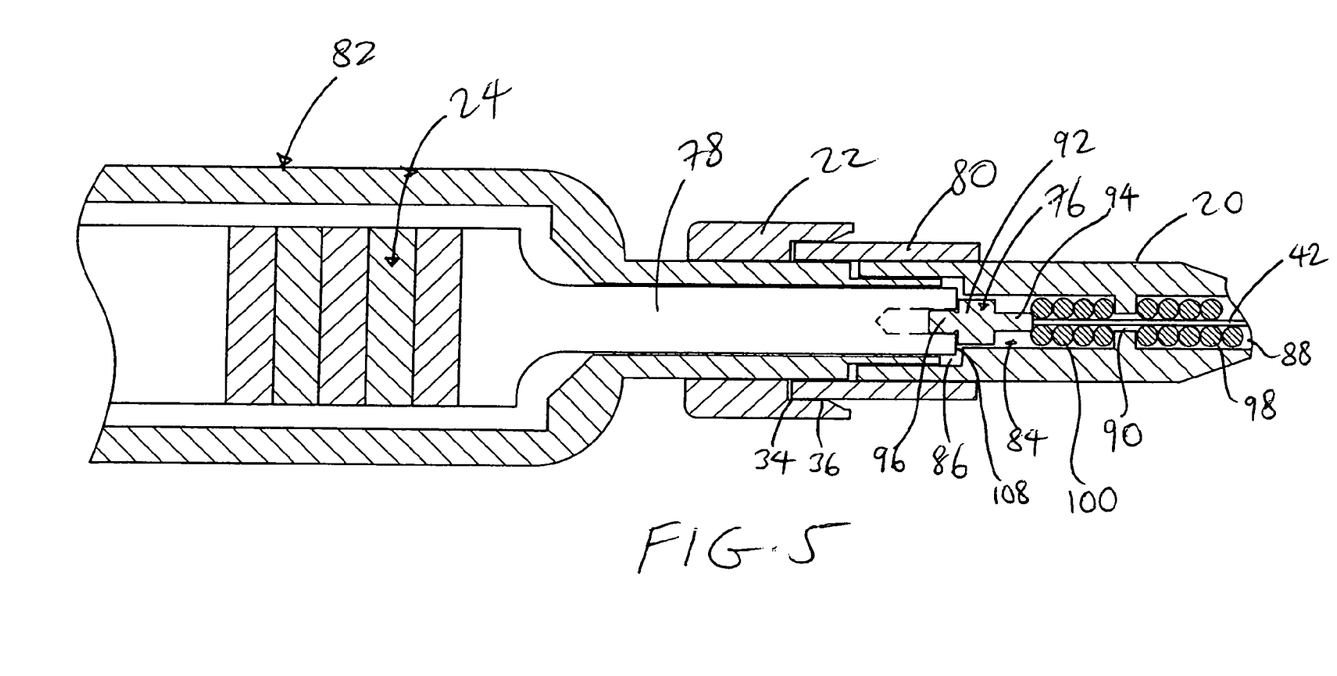
FIG. 5 is cross-sectional view of one embodiment of a sonic connector assembly that can be used with the system of FIG. 1.

Referring also to FIG. 5, the present invention further provides a sonic connector assembly that effectively connects the ultrasound transmission member 42 to the transducer 24 in a manner which reduces step sonic amplification and provides a smooth connection transition of the transmission member 42, thereby reducing the stress and fatigue experienced by the transmission member 42. The sonic connector assembly includes a sonic connector 76 that functions to grip or otherwise retain the proximal end of the ultrasound transmission member 42, and which can be removably connected to the transducer 24. In other words, the sonic connector 76 serves as an attaching element that couples the ultrasound transmission member 42 to the transducer 24 in a manner which minimizes transverse movement at the connection area while maintaining longitudinal ultrasound energy propagation. In this regard, longitudinal vibrations are desirable, while transverse vibrations may cause breakage in the ultrasound transmission member 42. The connection area between the ultrasound transmission member 42 and the transducer horn 78 is critical because the vibrational energy passes through this connection. At this highest displacement point, longitudinal vibrations produce antinodes (maximum displacement/minimum stress), while transverse vibrations produce a node or area of maximum stress. Since the greatest amount of transverse motion occurs at the connection area between the ultrasound transmission member 42 and the transducer horn 78, and because the cross-section of the ultrasound transmission member 42 is small, reduction of transverse movements at the connection area between the ultrasound transmission member 42 and the transducer horn 78 is crucial in protecting the integrity of the ultrasound transmission member 42 and minimizing the potential for breakage of the ultrasound transmission member 42. Such transverse vibrations can be minimized by placing transverse absorbers along the ultrasound transmission member 42 at the connection area between the ultrasound transmission member 42 and the transducer horn 78, as described below.

In one embodiment illustrated in FIG. 5, the sonic connector assembly has a sonic connector 76 housed inside the proximal bore 84 of the catheter knob 20. The proximal bore 84 has a rear section 86 that has a proximal opening into which the transducer horn 78 may be inserted to engage the sonic connector 76. A distal bore 88 is provided at the distal end of the catheter knob 20, with the distal bore 88 communicating with the proximal bore 84 via a channel 90. The sonic connector 76 has a front shaft 94 extending distally from a central portion 92. The sonic connector 76 also has a threaded stem 96 extending proximally from the central portion 92 to permit the distal end of the transducer horn 78 to be threadably screwed onto and removably attached to the sonic connector 76. The proximal end of the Y-connector 18 can be threadably engaged to the distal opening of the distal bore 88.

The distal end of the front shaft 94 has an inner bore (not shown) that terminates before the central portion 92. The proximal end of the ultrasound transmission member 42 extends through the channel 90 in the knob 20 and through the bores 84 and 88, and is dimensioned to be snugly fitted inside the inner bore of the front shaft 94. The proximal end of the ultrasound transmission member 42 is secured inside the inner bore of the front shaft 94 by welding, bonding, crimping, soldering, or other conventional attachment mechanisms.

A first absorber 98 is seated in the distal bore 88 and has a bore that receives (i.e., circumferentially surrounds) the ultrasound transmission member 42. A second absorber 100 is seated in the proximal bore 84 and has a bore that receives (i.e., circumferentially surrounds) the ultrasound transmission member 42. In other words, each absorber 98 and 100 is positioned between the ultrasound transmission member 42 and its respective bore 88 and 84. The absorbers 98, 100 can be made of an elastic material, and non-limiting examples include a polymer or rubber. Alternatively, the absorbers 98, 100 can be provided in the form of O-rings. The absorbers 98 and 100 function to absorb transverse micro-motions, thereby minimizing the undesirable transverse vibrations.

Figure 6:
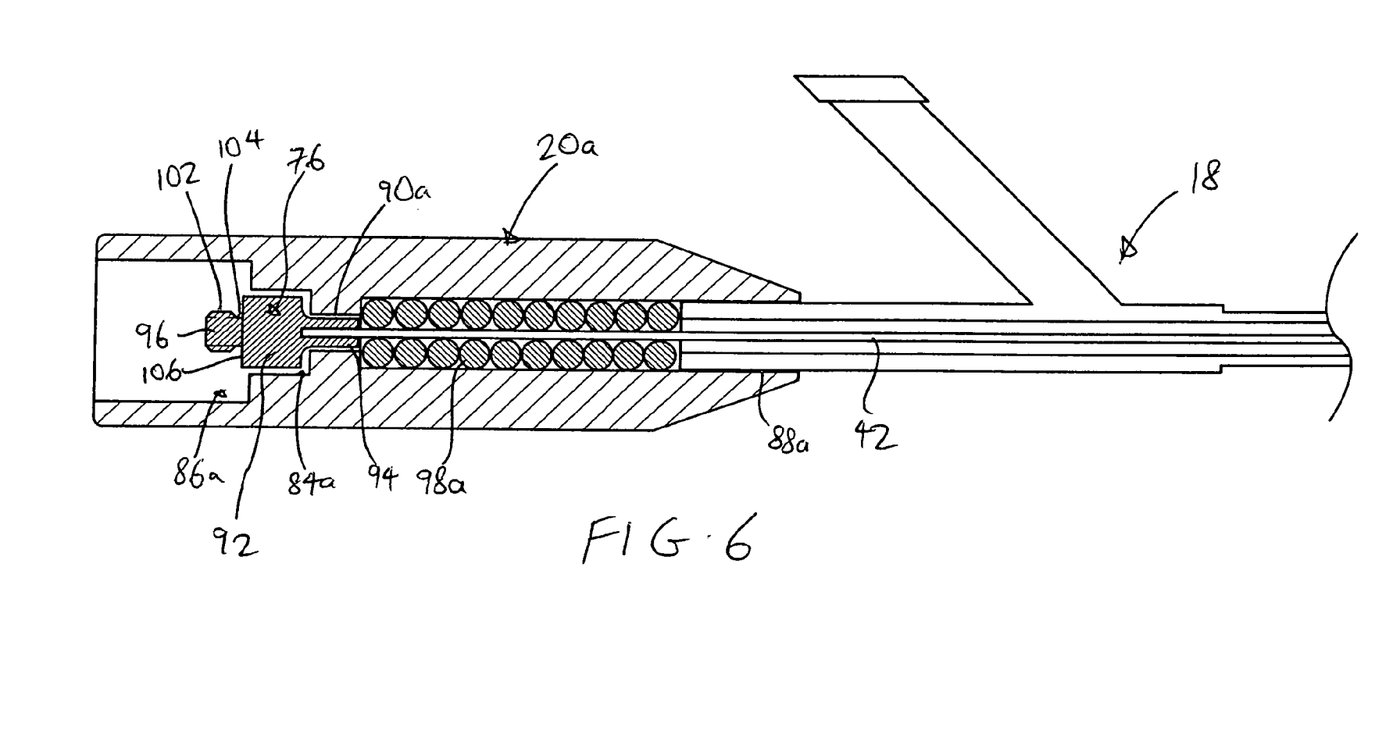
FIG. 6 is cross-sectional view of another embodiment of a sonic connector assembly that can be used with the system of FIG. 1.

FIG. 6 illustrates how the sonic connector 76 shown in FIG. 5 can be used with a slightly different configuration of the catheter knob 20. The catheter knob 20a in FIG. 6 has a proximal bore 84a with a rear section 86a, and a channel 90a that connects the proximal bore 84a to a distal bore 88a. The ultrasound transmission member 42 extends through the Y-connector 18, and through the distal bore 88a, the channel 90a and the proximal bore 84a. The sonic connector 76 is seated in the proximal bore 84a with the front shaft 94 of the sonic connector 76 seated inside the channel 90a. An absorber 98a (which can be the same as absorbers 98 and 100 above) is seated in the distal bore 88a and has a bore that receives (i.e., circumferentially surrounds) the ultrasound transmission member 42. The proximal end of the Y-connector 18 can be threadably engaged to the distal opening of the distal bore 88a.

The sonic connector 76 shown in FIGS. 5 and 6 is provided with a partial thread and a flat proximal surface, which are important to providing a firm connection between the transducer horn 78 and the sonic connector 76. Specifically, referring to FIGS. 5 and 6, the threaded stem 96 has a thread 102 followed by a small unthreaded area 104 that separates the thread 102 from the proximal surface 106 of the central portion 92. This proximal surface is flat, and interfaces with the flat distal surface 108 of the transducer horn 78, thereby allowing a manual connection and disconnection (screw and unscrew) between the transducer horn 78 and the sonic connector 76.

Figure 7:
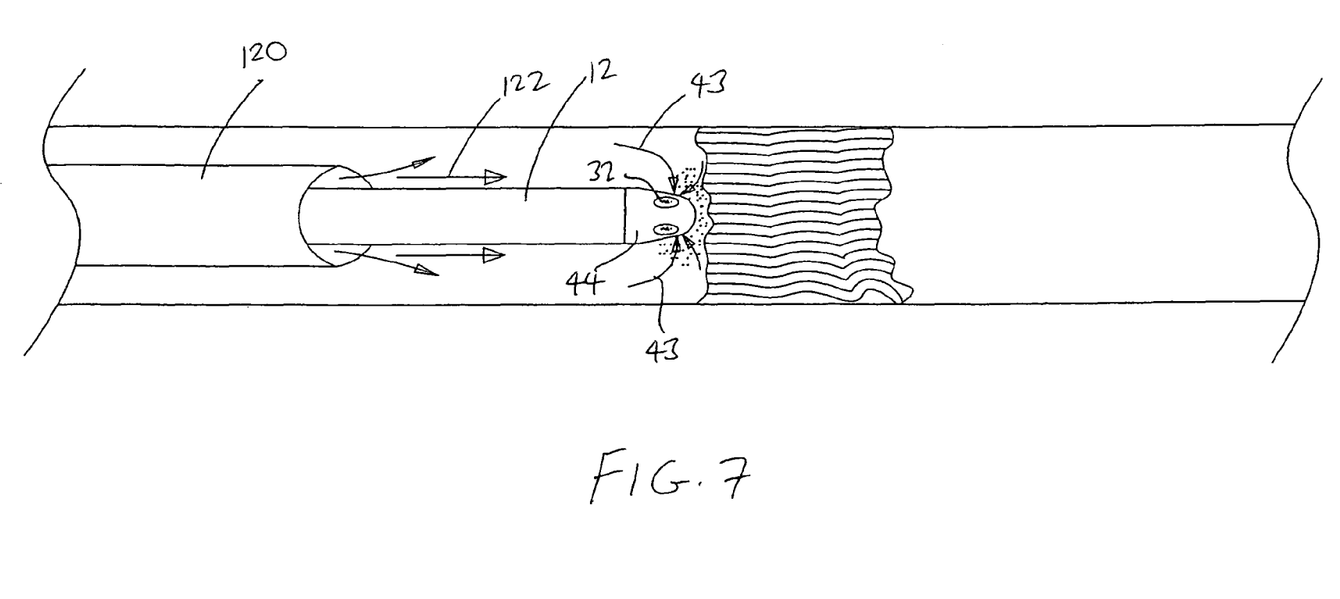
FIG. 7 illustrates reverse irrigation of the catheter of the system of FIG. 1.

The present invention further provides for simultaneous reverse irrigation and cooling. Particles generated during plaque ablation or angioplasty may cause stroke or heart attacks. As a result, removal of these particles is critical to the ultrasound procedure. According to the present invention, reverse irrigation can be used to remove particles that have been ablated during the ultrasound procedure. Referring to FIG. 7, irrigation fluid can be injected through a guiding catheter 120 (and along the outer surface of the catheter body 12) as shown by the arrows 122. The irrigation fluid will travel to the distal head 44 of the catheter 10, and will carry the particles through apertures 32 provided in the distal head 44 in a reverse direction (i.e., from distal to proximal) and through the main lumen 40. The irrigation fluid and particles will travel in a proximal direction inside the main lumen 40 to the Y-connector 18 and then on to the infusion tube 55, and is collected into a bottle or container that can be connected to the infusion tube 55. During this operation, the injection pump can serve as a negative pressure pump or vacuum to draw the particles through the main lumen 40 in a distal-to-proximal direction. The irrigant that is drawn through the main lumen 40 together with the particles will also serve as a simultaneous coolant for the ultrasound transmission member 42 and be removed via the infusion tube 55.

As yet a further alternative, the particles can be removed by applying a vacuum to remove the particles via the lumen of the guidewire tube 58. For example, in an "over-the-wire" catheter embodiment, particles can be removed via the lumen 60 of the guidewire tube 58 using a pump or a syringe.

The present invention also provides a method for local imaging of the region of the distal head 44 during an ultrasound procedure. The ability to inject contrast media to the distal tip of the catheter 10 and directly at or into the occlusion being treated provides significant clinical advantages. This injection can be performed through the main lumen 40, or in the case of an "over-the-wire" catheter, through the guidewire lumen 60. In the method for local imaging of the region of the distal head 44 during an ultrasound procedure, a physician can advance the catheter 10 to the site of the occlusion. Contrast media (such as those described above) can then be injected via the irrigation port 72 and through the main lumen 40, and exit through the apertures 32 in the distal head 44. For "over-the-wire" embodiments, the contrast media can exit through the guidewire lumen 58 and the distal section 68 of the central bore of the distal head 44. The contrast media would serve to confirm that the distal head 44 of the catheter 10 is at the proximal end of the occlusion (this step will be referred to hereinafter as a "contrast injection"). Energy can then be activated and the catheter 10 advanced into the occlusion. After an initial period of energization, the energy will be stopped, and another contrast injection performed through the catheter 10. With the distal head 44 of the catheter 10 into the occlusion, this will infuse the occlusion with contrast media and help the physician to visualize the vessel path, thereby reducing the risk of dissection and perforation. Energization and catheter advancement can then resume, alternating with contrast injections as required for diagnostic and navigational purposes. This process is continued until the catheter 10 has successfully facilitated guide wire advancement completely across the occlusion.

Figure 8:
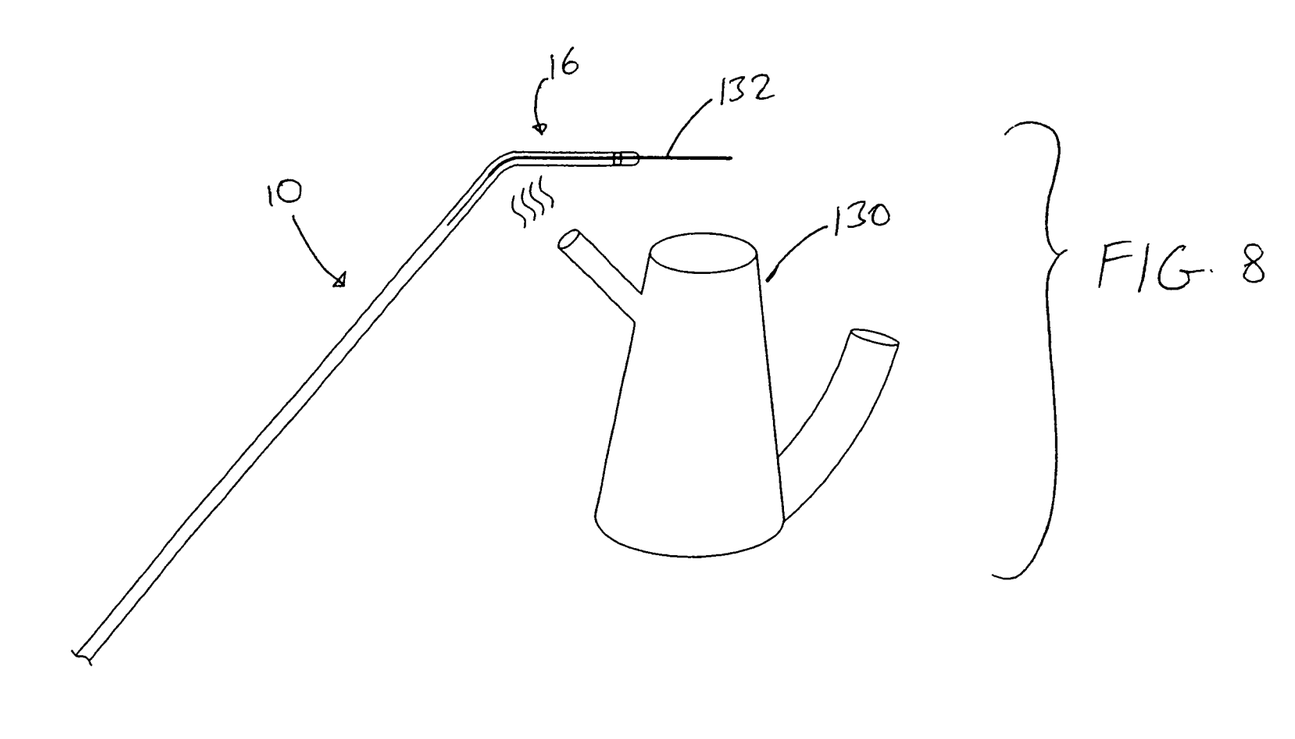
FIG. 8 illustrates shaping of the distal end of the catheter of the system of FIG. 1.

In addition, the distal end 16 of the catheter 10 can be custom shaped, either by the manufacturer, or by the end user in the catheter lab, in order to accommodate a specific anatomical situation for a particular patient. Polymers of construction for the catheter body 12 are selected such that their heat distortion temperatures are less than or equal to 100 degrees Celsius. Examples of such polymers include those from the Nylon family, including but not limited to all commercial grades of Pebax. Shaping can be accomplished by holding the distal end 16 of the catheter 10 in a bent configuration over a steam source 130 for several seconds, then cooling the distal end 16 at room temperature or by quenching the distal end 16 in a bath of saline or the like. The steam source 130 may be any conventional appliance such as an electric tea kettle (as shown in FIG. 8), a clothing steamer or the like. A hot air source may also be used (such as a hair dryer), but a steam source is preferred because the temperature will be more repeatable. This shaping process is applied to the polymer material of the catheter body 12. However, it may also include shaping the distal end of the ultrasound transmission member 42. As set forth above, the ultrasound transmission member may be made of a nickel titanium alloy, which typically exhibits superelastic properties in a martensitic stage. Thus, heating the distal and of the ultrasound transmission member 42 or the distal end of the catheter body 12 above the martensitic stage temperature will transform it to an austenitic stage. Bending the distal end of the entire catheter body 12 to a desirable shape is much easier to achieve in the austenitic stage. A return of the shaped portion of the transmission member 42 or distal end of the catheter body 12 to the martensitic stage will create a permanent bend that still will exhibit superelastic characteristics similar to the other portion of the transmission member 42.

A customized shape of the distal end of the ultrasound catheter 10 can also be achieved by shaping the distal end of the ultrasound transmission member 42 prior to the final assembly. Shaping can be accomplished by carefully bending the distal end of the ultrasound transmission member 42 using, for example, a mandrel and inducing a mechanical deformation on its distal end until a desired permanent shape is achieved, similar to methods used to shape conventional guidewires. It is important that the bend is longer and smooth without sudden angulations or dents, so that ultrasound energy propagation will not cause stress concentration areas and potential breakage of the ultrasound transmission member. Then, the shaped distal end of the transmission member 42 is placed inside the catheter body 12 which will assume a shape that corresponds to the shape of the shaped ultrasound transmission member. To facilitate shaping, the distal end of an ultrasound transmission member 42 made of a superelastic alloy may be pre-heated above the martensitic temperature transformation. Heating the ultrasound transmission member 42 to a desired shape or angle will transform the alloy from the martensitic stage to the austenitic stage and facilitate the shaping process. After cooling at room temperature, the shaped portion of the transmission member 42 will permanently retain a new desired angulation.

Figure 9A:
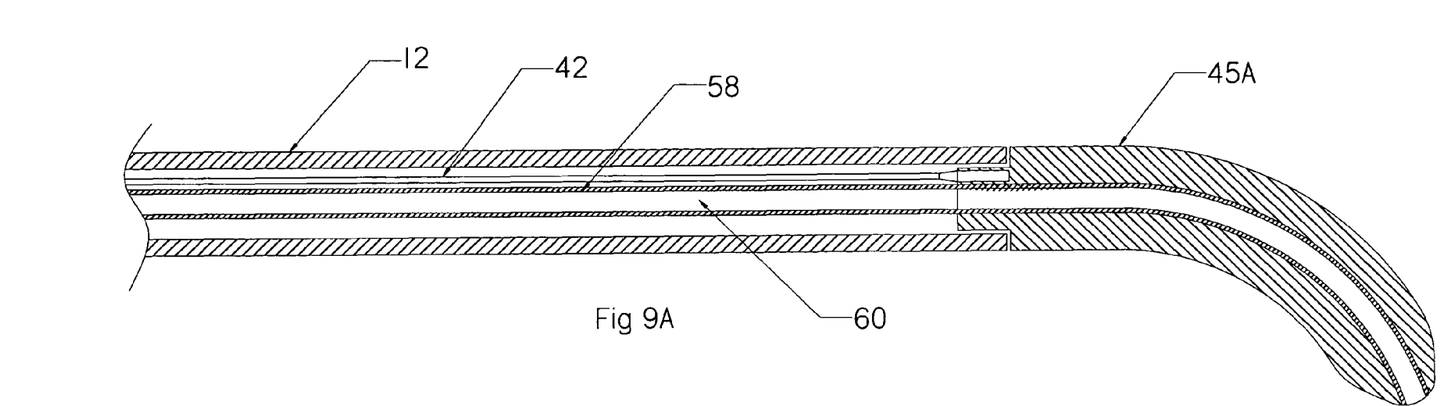
FIG. 9A is a cross-sectional view of the distal end of another catheter that can be used with the system of FIG. 1, with the distal head being pre-shaped at a desired angle.

FIG. 9A shows a pre-shaped distal head 45a of the ultrasound catheter 10 that can be achieved by making the distal head longer when compared to the distal head 44 shown in FIGS. 4A and 4B. A longer distal head 45a of the ultrasound catheter 10 that is bent at a desired angle is attached to the distal end of the transmission member 42. Any bend or shape of the distal head 45a may be achieved using conventional mechanical methods, or any of the methods described above. The length of the distal head may be within the range from 0.5 mm to 10 cm, and preferably, from 2 mm to 2 cm. Angulations of the bend may vary anywhere between 1-90 degrees depending on the complexity of the anatomy, and the physician's preferences.

Figure 9B:
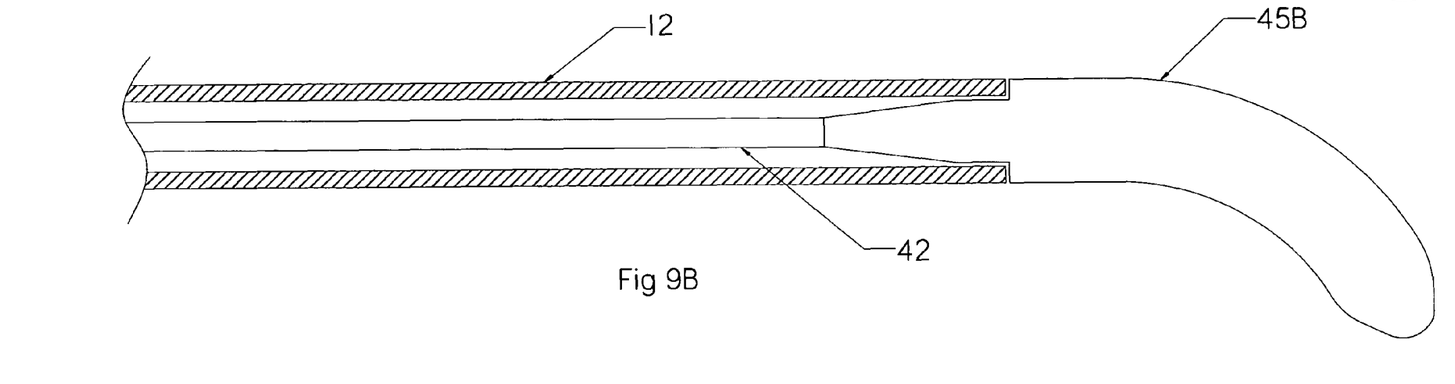
FIG. 9B is a cross-sectional view of the distal end of another catheter that can be used with the system of FIG. 1, with the ultrasound transmission member serving as the distal head and being pre-shaped at a desired angle.

FIG. 9B shows a pre-shaped distal end of an ultrasound catheter that has no guidewire capability. The distal end 45b of the transmission member 42 serves as the distal head of the catheter. Pre-shaping of the distal end 45b of the ultrasound transmission member 42 may be achieved using mechanical or mechanical and thermal methods, or any of the methods described above.

Bending or pre-shaping of the distal end of the ultrasound catheter 10 is important in navigating difficult anatomies. Angulations of the bends may also vary anywhere between 1-90 degrees depending on the anatomy and the complexities involved. These bends and angulations of the distal end of the ultrasound catheter 10 are equally important to navigate difficult anatomies for ultrasound catheters which operate with or without a guidewire.

A ductile wire 132 may be placed in the distal end of the catheter's main lumen 40 prior to shaping. This serves two purposes: The wire 132 will support and prevent kinking of the catheter body 12 when it is bent, and the wire 132 will also hold the catheter body 12 in a desired shape during the shaping process.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound catheter, comprising:
    an elongated flexible catheter body having a proximal end, a distal end, and a lumen extending longitudinally therethrough;
    an ultrasound transmission member extending along a longitudinal axis through the lumen of the catheter body and having a distal end; and
    a non-bulbous distal head extending from the distal end of the ultrasound transmission member and having a bent pre-shaped portion, the bent pre-shaped portion being disposed on a distal side of the catheter body and having a curvilinear central axis along a length of the bent pre-shaped portion, the bent pre-shaped portion having a cross section that is perpendicular to the central axis and curves away from the longitudinal axis along the length of the bent pre-shaped portion.

2. The catheter of claim 1, wherein the distal head is angulated at an angle between 5-90 degrees.

3. The catheter of claim 1, further including a guidewire lumen extending longitudinally through a portion of the lumen and through the distal head.

4. The catheter of claim 3, wherein the guidewire lumen terminates in a guidewire port that is adjacent the proximal end of the catheter body.

5. The catheter of claim 3, wherein the guidewire lumen terminates in a guidewire port that is closer to the distal end of the catheter body than to the proximal end of the catheter body.

6. The catheter of claim 3, wherein the guidewire lumen is defined by a separate guidewire tube.

7. The catheter of claim 6, wherein the guidewire tube is positioned within the lumen of the catheter body.

8. The catheter of claim 3, wherein the catheter body has two lumens, with one lumen receiving the ultrasound transmission member and the other lumen receiving the guidewire.

9. The catheter of claim 3, wherein the guidewire lumen is defined by a guidewire tube that is affixed to the distal head.

10. The catheter of claim 9, wherein the guidewire lumen has a proximal end and a distal end, and wherein the proximal end of the guidewire lumen terminates adjacent the proximal end of the catheter body and is affixed to the catheter body.

11. The catheter of claim 3, wherein the guidewire lumen has a proximal end and a distal end, and wherein the proximal end of the guidewire lumen terminates adjacent the proximal end of the catheter body and is affixed to the catheter body.

12. The catheter of claim 1, wherein the bent pre-shaped portion of the distal head has a length ranging from 0.5 mm to 10 cm.

13. The catheter of claim 12, wherein the bent pre-shaped portion of the distal head has a length ranging from 2 mm to 2 cm.

\* \* \* \* \*